US 7,910,785 B2

(12) United States Patent
Roth et al.

(10) Patent No.: US 7,910,785 B2
(45) Date of Patent: Mar. 22, 2011

(54) HYDROCARBON CONVERSION PROCESS USING EMM-10 FAMILY MOLECULAR SIEVE

(75) Inventors: Wieslaw J. Roth, Sewell, NJ (US); Jane C. Cheng, Bridgewater, NJ (US); Mohan Kalyanaraman, Media, PA (US); Michael C. Kerby, Houston, TX (US); Terry E. Helton, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 426 days.

(21) Appl. No.: 11/960,422

(22) Filed: Dec. 19, 2007

(65) Prior Publication Data
US 2009/0163753 A1 Jun. 25, 2009

Related U.S. Application Data

(63) Continuation-in-part of application No. 11/823,129, filed on Jun. 27, 2007, and a continuation-in-part of application No. 11/824,742, filed on Jul. 2, 2007.

(60) Provisional application No. 60/834,031, filed on Jul. 28, 2006, provisional application No. 60/834,032, filed on Jul. 28, 2006, provisional application No. 60/926,204, filed on Apr. 25, 2007, provisional application No. 60/834,030, filed on Jul. 28, 2006, provisional application No. 60/834,001, filed on Jul. 28, 2006.

(51) Int. Cl.
*C07C 2/66* (2006.01)
(52) U.S. Cl. ...................................... 585/467; 585/323
(58) Field of Classification Search .................. 585/467, 585/323
See application file for complete search history.

(56) References Cited

U.S. PATENT DOCUMENTS

| 4,439,409 A | 3/1984 | Puppe et al. |
| 4,826,667 A | 5/1989 | Zones et al. |
| 4,891,458 A | 1/1990 | Innes et al. |
| 4,954,325 A | 9/1990 | Rubin et al. |
| 4,992,606 A | 2/1991 | Kushnerick et al. |
| 5,077,445 A * | 12/1991 | Le .................................. 585/467 |
| 5,236,575 A | 8/1993 | Bennett et al. |
| 5,334,795 A | 8/1994 | Chu et al. |
| 5,362,697 A | 11/1994 | Fung et al. |
| 6,077,498 A | 6/2000 | Diaz Cabanas et al. |
| 2006/0020154 A1 | 1/2006 | Lo et al. |
| 2008/0027256 A1 | 1/2008 | Roth et al. |
| 2008/0027259 A1 | 1/2008 | Roth et al. |

FOREIGN PATENT DOCUMENTS

| WO | 2007/130055 | 11/2007 |
| WO | 2008/013639 | 1/2008 |

OTHER PUBLICATIONS

Lee, Song-Ho et al., "*Reinvestigation into the synthesis of Zeolites Using Diquaternary Alkylammonium Ions $(CH_3)3N+(CH_2)nN+(CH_3)3$ with n=3-10 as Structure-directing Agents*", Microporous and Mesoporous Materials, 2004, vol. 68, pp. 97-104.

Lee, Song-Ho et at., "*Synthesis of Zeolite MCM-22 Using $N,N,N^1,N^1,N^1$ Hexamethyl-1,5-Pentanediaminium and Alkali Metal Cations as Structure-directing Agents*", Chemistry Letters, 2003, vol. 32, No. 6, pp. 542-543.

U.S. Appl. No. 11/823,129, filed Jun. 27, 2007, Inventor: Wieslaw J. Roth, et al., entitled Molecular Sieve Composition (EMM-10-P), Its Method Of Making, And Use For Hydrocarbon Conversions.

U.S. Appl. No. 11/827,953, filed Jul. 13, 2007, Inventor: Wieslaw J. Roth, et al., entitled A Novel Molecular Sieve Composition, A Method Of Making And A Process Of Using The Same.

U.S. Appl. No. 11/824,742, filed Jul. 2, 2007, Inventor: Wieslaw J. Roth et al., entitled Molecular Sieve Composition (EMM-10, Its Method Of Making, And Use For Hydrocarbon Conversions.

* cited by examiner

*Primary Examiner* — Thuan Dinh Dang
(74) *Attorney, Agent, or Firm* — Darryl M. Tyus; Xiaobing Feng

(57) ABSTRACT

This disclosure relates to a process for hydrocarbon conversion comprising contacting, under conversion conditions, a feedstock suitable for hydrocarbon conversion with a catalyst comprising an EMM-10 family molecular sieve.

12 Claims, No Drawings

_US 7,910,785 B2_

HYDROCARBON CONVERSION PROCESS USING EMM-10 FAMILY MOLECULAR SIEVE

CROSS-REFERENCE TO RELATED APPLICATIONS

This application is a Continuation-in-Part of U.S. Application Ser. No. 11/823,129, filed 27 Jun. 2007, which claims priorities to U.S. Provisional Application No. 60/834,030, filed 28 Jul. 2006, U.S. Provisional Application No. 60/834,031, filed 28 Jul. 2006, U.S. Provisional Application No. 60/926,204, filed 25 Apr. 2007, and U.S. Provisional Application No. 60/834,001, filed on 28 Jul. 2006. This Application is also a Continuation-in-Part of U.S. application Ser. No. 11/824,742, filed 2 Jul. 2007, which claims priorities to U.S. Provisional Application Ser. No. 60/834,031, filed 28 Jul. 2006, U.S. Provisional Application No. 60/834,032, filed 28 Jul. 2006, and U.S. Provisional Application No. 60/926,204, filed 25 Apr. 2007, all of which are incorporated by reference in their entireties.

FIELD OF THE INVENTION

The present disclosure relates to a hydrocarbon conversion process using EMM-10 family molecular sieve.

BACKGROUND OF THIS DISCLOSURE

Molecular sieve materials, both natural and synthetic, have been demonstrated in the past to have catalytic properties for various types of hydrocarbon conversion. Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a reaction mixture for hydrothermal reaction containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a reaction mixture for hydrothermal reaction containing an adamantane quaternary ammonium ion. U.S. Pat. No. 6,077,498 refers to a crystalline molecular sieve composition of matter named ITQ-1 and its synthesis from a reaction mixture for hydrothermal reaction containing one or a plurality of organic additives.

U.S. patent application Ser. No. 11/823,129, the entire content of which is fully incorporated by reference, discloses a crystalline molecular sieve, in its as-synthesized form, identified as EMM-10-P, a method of making EMM-10-P. In some embodiments of the U.S. patent application Ser. No. 11/823,129, the EMM-10-P has, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms. In addition, the X-ray diffraction pattern of the EMM-10-P may further include two XRD distinguishable peaks with d-spacing maxima at 11.06±0.18 and 9.25±0.13 Angstroms, wherein the peak intensity of the d-spacing maximum at 11.06±0.18 Angstroms is at least as great as the peak intensity of the d-spacing maximum at 9.25±0.13 Angstroms. Additionally, the peaks with d-spacing maxima at 11.06±0.18 and 9.25±0.13 Angstroms may be non-discrete peaks.

U.S. patent application Ser. No. 11/824,742, the entire content of which is fully incorporated by reference, disclose novel molecular sieves designated as EMM-10, and the method making the same. In some embodiments of U.S. patent application Ser. No. 11/824,742, the EMM-10, in its ammonium exchanged form or in its calcined form, comprises unit cells with MWW topology, the crystalline molecular sieve is characterized by diffraction streaking from the unit cell arrangement in the c direction. In addition, the EMM-10 may further be characterized by the arced hk0 patterns of electron diffraction pattern. In further additional embodiments of the U.S. patent application Ser. No. 11/824,742, the EMM-10 may further be characterized by the unit cells streaking along c direction.

U.S. patent application Ser. No. 11/827,953, the entire content of which is fully incorporated by reference, discloses a crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms.

A molecular sieve composition as described or characterized in U.S. patent application Ser. Nos. 11/823,129, 11/824,742, and/or 11/827,953 is designated as an EMM-10 family molecular sieve as used herein this disclosure.

Many aromatic hydrocarbons are valuable commercial products. For example, benzene (Bz), para-xylene (PX), ethylbenzene (EB), cumene, and sec-butylbenzene (S-BB) are very valuable commercial products.

Aromatic compounds can be formed by converting non-aromatic compounds to aromatic compounds. An example of such a conversion is the dehydrocyclo-oligomerization of aliphatic hydrocarbons to form aromatics. This process typically uses an intermediate pore size zeolite catalyst such as ZSM-5. Another process for converting non-aromatic compounds to aromatic compounds involves reforming where $C_6$ and higher carbon number reactants, primarily paraffins and naphthenes, are converted to aromatic compounds. This process typically uses monofunctional large pore zeolites, such as zeolites L, Y, and X or bifunctional catalysts which can comprise a metal oxide support acidified by a halogen.

Also, less valuable aromatic compounds can be converted into more valuable aromatic compounds. Examples of such processes include the methylation of toluene to form xylenes, the disproportionation of toluene to form xylenes and benzene, the alkylation of benzene to produce ethylbenzene, cumene, or sec-butylbenzene, and the isomerization of xylene feedstock to produce a product enriched in para-xylene. These processes typically use a catalyst comprising a molecular sieve, such as ZSM-5, MCM-22, and/or zeolite beta.

The alkylation of aromatic hydrocarbon compounds employing zeolite catalysts is known and understood in the art. U.S. Pat. No. 5,334,795 describes the liquid phase alkylation of benzene with ethylene in the presence of MCM-22 to produce ethylbenzene; and U.S. Pat. No. 4,891,458 discloses liquid phase alkylation and transalkylation processes using zeolite beta.

Zeolite-based catalysts are used in the alkylation of benzene with propylene to produce cumene. U.S. Pat. No. 4,992,606 discloses a process for preparing cumene using MCM-22 in liquid phase.

This invention relates to a process for using the EMM-10 family molecular sieve in the process of hydrocarbon conversion, such as, alkylation, transalkylation, olefin oligomerization, hydrocarbon cracking, olefin removal, disproportionation, separation, and adsorption. In particular, this disclosure relates to aromatic alkylation to produce ethylbenzene (EB), cumene, and sec-butylbenzene (S-BB), olefin removal from aromatic feedstock, and olefin oligomerization processes such as gasoline.

We surprisingly find that the EMM-10 family molecular sieve has different performance as comparing with the known MCM-22 molecular sieve. Also, the EMM-10 family molecular sieve has manufacturing advantage over the known MCM-22 molecular sieve because of the different template for the manufacturing process.

SUMMARY OF THIS DISCLOSURE

In some embodiments, this disclosure relates to a process for hydrocarbon conversion, preferably aromatic conversion, comprising contacting, under conversion conditions, a feedstock suitable for hydrocarbon conversion with a catalyst comprising an EMM-10 family molecular sieve, preferably EMM-10.

In preferred embodiments, the hydrocarbon conversion is a process for alkylating an aromatic hydrocarbon with an alkylating agent to produce an alkylated aromatic product, the process comprising:

(a) contacting the aromatic hydrocarbon and the alkylating agent with the catalyst composition of any one of claims 1, 2, 8, and 10 under alkylation conditions effective to alkylate the aromatic hydrocarbon with the alkylating agent to form an effluent comprising the alkylated aromatic product, wherein the alkylated aromatic product comprises monoalkylated aromatic compound and polyalkylated aromatic compound.

In one aspect of the process for alkylating an aromatic hydrocarbon with an alkylating agent to produce an alkylated aromatic product, the aromatic hydrocarbon comprises benzene, the alkylating agent comprises ethylene, and the alkylated aromatic product comprises ethylbenzene.

In another aspect of the process for alkylating an aromatic hydrocarbon with an alkylating agent to produce an alkylated aromatic product, the aromatic hydrocarbon comprises benzene, the alkylating agent comprises propylene, and the alkylated aromatic product comprises cumene.

In yet another aspect of the process for alkylating an aromatic hydrocarbon with an alkylating agent to produce an alkylated aromatic product, the aromatic hydrocarbon comprises benzene, the alkylating agent comprises butene, and the alkylated aromatic product comprises sec-butylbenzene.

In further aspect of the process for alkylating an aromatic hydrocarbon with an alkylating agent to produce an alkylated aromatic product, the process further comprises steps of:

(b) separating the polyalkylated aromatic compound from the effluent; and (c) contacting the polyalkylated aromatic compound with an alkylating agent under transalkylation conditions.

In other embodiments of this disclosure, the hydrocarbon conversion comprises a process of removing bromine-reactive contaminates in a hydrocarbon feedstock. In one aspect, the hydrocarbon feed has a multi-olefin level of less than 500 wppm.

In some aspect of the hydrocarbon conversion, the hydrocarbon conversion conditions comprises a temperature of from about 200° C. to about 760° C., a pressure of from about 101 kPa-a to about 20000 kPa-a, and a weight hourly space velocity of from about 0.08 to about 2000 $hr^{-1}$.

In some preferred the aromatics conversion embodiments, the aromatics conversion comprises converting feedstock comprising aromatic compounds to a product comprising aromatic compounds which differ from the feedstock.

DETAILED DESCRIPTION

Introduction

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "hydrocarbon conversion", as used herein, shall mean the production of hydrocarbon by the conversion of non-hydrocarbons to hydrocarbon compounds. The term "hydrocarbon conversion", as used herein, shall also include the conversion of feedstock comprising hydrocarbon compounds to a product comprising hydrocarbon compounds which differ from the feedstock. The term "hydrocarbon conversion", as used herein, shall further include the selective adsorption of hydrocarbons, e.g., alkyl substituted benzenes such as xylenes, for the purpose of separating various isomers of the hydrocarbons, e.g., separation of para-xylene from ortho-xylene and meta-xylene.

The term "aromatics conversion", as used herein, shall mean the production of aromatics by the conversion of non-aromatic hydrocarbons to aromatic compounds. The term "aromatics conversion", as used herein, shall also include the conversion of feedstock comprising aromatic compounds to a product comprising aromatic compounds which differ from the feedstock. The term "aromatics conversion", as used herein, shall further include the selective adsorption of aromatic hydrocarbons, e.g., alkyl substituted benzenes such as xylenes, for the purpose of separating various isomers of the aromatic hydrocarbons, e.g., separation of para-xylene from ortho-xylene and meta-xylene.

As used herein, an "alkylatable aromatic compound" is a compound that may receive an alkyl group and an "alkylating agent" is a compound which may donate an alkyl group.

The term "wppm" as used herein is defined as parts per million by weight.

All weights of molecular sieve, weights of binder, and weights of catalyst composition, as used in this disclosure, are calcined based weight (at 540° C. in air for at least one hour).

The term "aromatic" as used herein is to be understood in accordance with its art-recognized scope which includes alkyl-substituted and unsubstituted mono- and polynuclear compounds. Compounds of an aromatic character, which possess a heteroatom, are also useful provided sufficient activity can be achieved if they act as catalyst poisons under the reaction conditions selected. A non-exclusive list of examples of aromatic compounds includes benzene and toluene.

The term "MCM-22 family material" (or "material of the MCM-22 family" or "molecular sieve of the MCM-22 family"), as used herein, includes:
  (i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;
  (ii) molecular sieves made from a common second degree building block, a 2-dimensional tiling of such MWW framework type unit cells, forming a "monolayer of one unit cell thickness", preferably one c-unit cell thickness;
  (iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or
  (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), UZM-8 (described in U.S. Pat. No. 6,756,030), and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, UZM-8, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). Typical examples of the non-MCM-22 family molecular sieve(s) co-existing with the MCM-22 family molecular sieve(s) of this disclosure are Kenyaite, EU-1, ZSM-50, ZSM-12, ZSM-48, ZSM-5, Ferrierite, Mordenite, Sodalite, and/or Analcine. Other examples of the non-MCM-22 family molecular sieve(s) co-existing with the MCM-22 family molecular sieve(s) of this disclosure are molecular sieves having framework type of EUO, MTW, FER, MOR, SOD, ANA, and/or MFI. The MCM-22 family materials of this disclosure are preferably substantially free of non-MCM-22 family material(s). The term "substantially free of non-MCM-22 family material(s)" used herein means the MCM-22 family material of this disclosure preferably contains a minor proportion (less than 50 wt %), preferably less than 20 wt %, of non-MCM-22 family materials ("impurities") in the MCM-22 family materials, which weight percent (wt %) values are based on the combined weight of impurities and pure phase MCM-22 family materials.

Catalyst

The catalyst composition of this disclosure comprises an EMM-10 family molecular sieve.

The EMM-10 family molecular sieve comprises at least one of the materials as disclosed in U.S. patent application Ser. Nos. 11/823,129, 11/824,742, and 11/827,953.

The EMM-10 family molecular sieve as disclosed in U.S. patent application Ser. No. 11/823,129 is EMM-10-P. An EMM-10-P molecular sieve is a crystalline molecular sieve having, in its as-synthesized form, an X-ray diffraction pattern including d-spacing maxima at 13.18±10.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms.

In addition, the X-ray diffraction pattern of the EMM-10-P molecular sieve may further include two XRD distinguishable peaks with d-spacing maxima at 11.06±0.18 and 9.25±0.13 Angstroms, wherein the peak intensity of the d-spacing maximum at 11.06±0.18 Angstroms is at least as great as the peak intensity of the d-spacing maximum at 9.25±0.13 Angstroms. Additionally, the peaks with d-spacing maxima at 11.06±0.18 and 9.25±0.13 Angstroms may be non-discrete peaks.

In a preferred embodiment, the EMM-10-P molecular sieve is a crystalline MCM-22 family molecular sieve that has a total surface area of greater than 450 m$^2$/g as measured by the N$_2$ BET method. The crystalline MCM-22 family molecular sieve of EMM-10-P preferably has a ratio of the external surface area over the total surface area of less than 0.15 after conversion into H-form by exchange with ammonium nitrate and calcination, wherein the external surface area is determined from a t-plot of the N$_2$ BET.

In yet further additional embodiments, the EMM-10-P molecular sieve has a morphology of tabular habit, wherein at least 50 wt % of the EMM-10-P molecular sieve have a crystal diameter greater than 1 μm as measured by the SEM, preferably greater than 2 μm as measured by the SEM.

In some aspects, the EMM-10-P molecular sieve has a morphology of tabular habit, wherein at least 50 wt % of the EMM-10-P molecular sieve have a crystal thickness of about 0.025 μm as measured by the SEM.

A method of making an EMM-10-P molecular sieve comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity, preferably 10 to 10000, more preferably from 10 to 55;
H$_2$O:Y=1 to 10000, preferably 1 to 5000, more preferably from 5 to 35;
OH$^-$:Y without trivalent element source correction=0.001 to 0.59, and/or OH$^-$:Y (with trivalent element source correction)=0.001 to 0.39
M$^+$:Y=0.001 to 2, preferably from 0.1 to 1;
R:Y=0.001 to 2, preferably from 0.1 to 1;
wherein M is an alkali metal and R is at least one N,N,N,N'N'N'-hexamethyl-1,5-pentanediaminium salt (Me$_6$-diquat-5 salt(s)), preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, Me$_6$-diquat-5 hydroxide bromide, Me$_6$-diquat-5 hydroxide chloride, Me$_6$-diquat-5 hydroxide fluoride, Me$_6$-diquat-5 hydroxide iodide, Me$_6$-diquat-5 hydroxide nitrate, Me$_6$-diquat-5 fluoride bromide, Me$_6$-diquat-5 fluoride chloride, Me$_6$-diquat-5 fluoride iodide, Me$_6$-diquat-5 fluoride nitrate, Me$_6$-diquat-5 chloride bromide, Me$_6$-diquat-5 chloride iodide, Me$_6$-diquat-5 chloride nitrate, Me$_6$-diquat-5 iodide bromide, Me$_6$-diquat-5 bromide nitrate, and any mixtures thereof, more preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, and any mixtures thereof, most preferably R is Me$_6$-diquat-5 dibromide; and
(b) submitting the mixture at crystallization conditions to form a product comprising the desired EMM-10-P molecular sieve, wherein the crystallization conditions comprise a temperature in the range of from 100° C. to 200° C., preferably from about 140 to about 180 C; and a crystallization time from about 1 hour to 400 hours, preferably from about 1 to 200 hours, optionally a stirring speed in the range of from 0 to 1000 RPM, preferably from 0 to 400 RPM.

Another method of making an EMM-10-P molecular sieve comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity, preferably 10 to 10000, more preferably from about 10 to 55;
H$_2$O:Y=1 to 10000, preferably 1 to 5000, more preferably from 5 to 35;
OH$^-$:Y without trivalent element source correction=0.61 to 0.72 and/or OH$^-$:Y with trivalent element source correction=0.41 to 0.49 or 0.51 to 0.62
M$^+$:Y=0.001 to 2, preferably from 0.1 to 1;
R:Y=0.001 to 2, preferably from 0.1 to 1;
wherein M is an alkali metal and R is at least one N,N,N,N'N'N'-hexamethyl-1,5-pentanediaminium salt (Me$_6$-diquat-5 salt(s)), preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, Me$_6$-diquat-5 hydroxide bromide, Me$_6$-diquat-5 hydroxide chloride, Me$_6$-diquat-5 hydroxide fluoride, Me$_6$-diquat-5 hydroxide iodide, Me$_6$-diquat-5 hydroxide nitrate, Me$_6$-diquat-5 fluoride bromide, Me$_6$-diquat-5 fluoride chloride, Me$_6$-diquat-5 fluoride iodide, Me$_6$-diquat-5 fluoride nitrate, Me$_6$-diquat-5 chloride bromide, Me$_6$-diquat-5 chloride iodide, Me$_6$-diquat-5 chloride nitrate, Me$_6$-diquat-5 iodide bromide, Me$_6$-diquat-5 bromide nitrate, and any mixtures thereof, more preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, and any mixtures thereof, most preferably R is Me$_6$-diquat-5 dibromide; and
(b) submitting the mixture at crystallization conditions to form a product comprising the desired EMM-10-P molecular sieve, wherein the crystallization conditions comprise a temperature in the range of from 100° C. to 200° C., preferably from about 140 to about 180 C; and a crystallization time from about 1 hour to 400 hours, preferably from about 1 to 200 hours, optionally a stirring speed in the range of from 0 to 1000 RPM, preferably from 0 to 400 RPM.

Yet another method of making an EMM-10-P molecular sieve comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:

Y:X$_2$=10 to infinity, preferably 10 to 10000, more preferably from 10 to 55;

H$_2$O:Y=1 to 35, preferably from 5 to 35;

OH$^-$:Y=0.001 to 2, preferably from 0.01 to 0.5;

M$^+$:Y=0.001 to 2, preferably from 0.1 to 1;

R:Y=0.001 to 2, preferably from 0.1 to 1;

wherein M is an alkali metal and R is at least one N,N,N,N'N'N'-hexamethyl-1,5-pentanediaminium salt (Me$_6$-diquat-5 salt(s)), preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, Me$_6$-diquat-5 hydroxide bromide, Me$_6$-diquat-5 hydroxide chloride, Me$_6$-diquat-5 hydroxide fluoride, Me$_6$-diquat-5 hydroxide iodide, Me$_6$-diquat-5 hydroxide nitrate, Me$_6$-diquat-5 fluoride bromide, Me$_6$-diquat-5 fluoride chloride, Me$_6$-diquat-5 fluoride iodide, Me$_6$-diquat-5 fluoride nitrate, Me$_6$-diquat-5 chloride bromide, Me$_6$-diquat-5 chloride iodide, Me$_6$-diquat-5 chloride nitrate, Me$_6$-diquat-5 iodide bromide, Me$_6$-diquat-5 bromide nitrate, and any mixtures thereof, more preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, and any mixtures thereof, most preferably R is Me$_6$-diquat-5 dibromide, wherein the OH$^-$:Y is calculated with or without trivalent element source correction; and (b) submitting the mixture at crystallization conditions to form a product comprising the desired EMM-10-P molecular sieve, wherein the crystallization conditions comprise a temperature in the range of from 100° C. to 200° C., preferably from about 140 to about 180 C; and a crystallization time from about 1 hour to 400 hours, preferably from about 1 to 200 hours, optionally a stirring speed in the range of from 0 to 1000 RPM, preferably from 0 to 400 RPM.

The EMM-10 family molecular sieve as disclosed in U.S. patent application Ser. No. 11/824,742 is EMM-10. An EMM-10 molecular sieve is a crystalline molecular sieve, in its ammonium exchanged form or in its calcined form, comprising unit cells with MWW topology, the crystalline molecular sieve is characterized by diffraction streaking from the unit cell arrangement in the c direction.

In additional embodiments, the EMM-10 molecular sieve may further be characterized by the arced hk0 patterns of electron diffraction pattern.

In further additional embodiments, the EMM-10 molecular sieve may further be characterized by the unit cells streaking along c direction.

In yet further additional embodiments, the EMM-10 molecular sieve may further be characterized by the double unit cell along c direction.

In yet more embodiments, the EMM-10 molecular sieve is a crystalline MCM-22 family molecular sieve has a total surface area of greater than 450 m$^2$/g as measured by the N$_2$ BET method. The crystalline MCM-22 family molecular sieve has a ratio of the external surface area over the total surface area of less than 0.15 after conversion into H-form by exchange with ammonium nitrate and calcination, wherein the external surface area is determined from a t-plot of the N$_2$ BET.

In yet some additional embodiments, the EMM-10 molecular sieve may have a morphology of tabular habit, wherein at least 50 wt % of the EMM-10 molecular sieve having a crystal diameter greater than 1 μm as measured by the SEM.

In some aspect, the EMM-10 molecular sieve has a morphology of tabular habit, wherein at least 50 wt % of the EMM-10 molecular sieve having a crystal thickness of about 0.025 μm as measured by the SEM.

An EMM-10 molecular sieve may be made by recovering an EMM-P-10 molecular sieve followed by treating the recovered EMM-10-P molecular sieve by:

(1) ion-exchanging the EMM-10-P molecular sieve with an ammonium salt(s) solution;

(2) calcining the EMM-10-P molecular sieve under calcination conditions; or (3) ion-exchanging the EMM-10-P molecular sieve with an ammonium salt(s) solution and calcining the ion-exchanged EMM-10-P molecular sieve under calcination conditions.

The EMM-10 family molecular sieve as disclosed in U.S. patent application Ser. No. 11/827,953 is a crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms.

In some embodiments, the EMM-10 family molecular sieve as disclosed in U.S. patent application Ser. No. 11/827,953 may be made by a method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:

Y:X$_2$=10 to infinity

H$_2$O:Y=1 to 10000

OH$^-$:Y without trivalent element source correction=0.001 to 0.59, and/or OH$^-$:Y (with trivalent element source correction)=0.001 to 0.39

M$^+$:Y=0.001 to 2

R:Y=0.001 to 2 wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein the OH$^-$:Y is calculated; and (b) submitting the mixture at crystallization conditions to form a product comprising the desired crystalline molecular sieve, wherein the crystallization conditions comprise a temperature in the range of from 10° C. to 250° C., a stirring speed of ranging from at least 150 RPM to less than 5000 RPM, and a crystallization time from about 1 hour to 400 hours; and (c) recovering the crystalline molecular sieve.

In yet other embodiments, the EMM-10 family molecular sieve as disclosed in U.S. patent application Ser. No. 11/827,953 may be made by a method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity
H$_2$O:Y=1 to 10000
OH$^-$:Y without trivalent element source correction=0.74 to 2 and/or OH$^-$:Y with trivalent element source correction=0.64 to 2
M$^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein the OH$^-$:Y is calculated without trivalent element source correction; and
(b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and
(c) recovering the crystalline molecular sieve.

In yet other embodiments, the EMM-10 family molecular sieve as disclosed in U.S. patent application Ser. No. 11/827,953 may be made by a method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity
H$_2$O:Y=5 to 35
OH$^-$:Y=0.001 to 2
M$^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein the OH$^-$:Y is calculated with or without trivalent element source correction; and
(b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and
(c) recovering the crystalline molecular sieve.

In yet other embodiments, the EMM-10 family molecular sieve as disclosed in U.S. patent application Ser. No. 11/827,953 may be made by a method comprising the steps of:
(a) providing a mixture comprising at least one source of at least one tetravalent element (Y), at least one source of at least one alkali or alkali earth metal element, at least one directing-agent (R), water, at least one seed, and optionally at least one source of at least one trivalent element (X), the mixture having the following molar ratio:
Y:X$_2$=10 to infinity
H$_2$O:Y=1 to 10000
OH$^-$:Y=0.001 to 2
M$^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein the OH$^-$:Y is calculated with or without trivalent element source correction, wherein the seed has a concentration in the mixture ranging from about 0.01 to 10 wt% based on the weight of the tetravalent element oxide in the mixture; and
(b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and
(c) recovering the crystalline molecular sieve.

In yet other embodiments, the EMM-10 family molecular sieve as disclosed in U.S. patent application Ser. No. 11/827,953 may be made by a method comprising the steps of:
(a) providing a mixture comprising at least one source of at least one non-germanium tetravalent element (Y), at least one source of germanium (Ge), at least one directing-agent (R), water, and optionally at least one source of at least one trivalent element (X) and at least one source of at least one alkali or alkali earth metal element, the mixture having the following molar ratio:
(Ge+Y):X$_2$=10 to infinity
H$_2$O:Y=1 to 10000
M$^+$:Y=0 to 2
R:Y=0.001 to 2
wherein M is an alkali metal and R comprises at least one N,N,N,N'N'N'-hexamethyl-1,5-pentanediaminium salt(s), N,N,N,N'N'N'-hexamethyl-1,6-hexanediaminium salt(s), or any combination thereof; and
(b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and
(c) recovering the crystalline molecular sieve.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

Hydrocarbon Conversion Processes

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, pilling, pelletizing and extrusion, have been and are being used to produce macrostructures in the form of, for example, spherical particles, extrudates, pellets and Tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The EMM-10 family molecular sieve, preferably the EMM-10 molecular sieve, when employed either as an adsorbent or as a catalyst in an organic compound conversion process should be generally dehydrated, at least partially. This can be done by heating to a temperature in the range of e.g., 200° C. to 595° C. in an atmosphere such as air or nitrogen, and at atmospheric, sub-atmospheric or super-atmospheric pressures for e.g., between 30 minutes and 48 hours. The degree of dehydration is measured by the percentage of weight loss relative to the total weight loss of a molecular sieve sample at 595° C. under flowing dry nitrogen (less than 0.001 kPa partial pressure of water vapor) for 48 hours. Dehydration can also be performed at room temperature (~25° C.) merely by placing the silicate in a vacuum, but a longer time is required to obtain a sufficient amount of dehydration.

The EMM-10 family molecular sieve especially in its metal, hydrogen and ammonium forms can be beneficially converted to another form by thermal treatment. This thermal treatment is generally performed by heating one of these forms at a temperature of at least 370° C. for at least 1 minute and generally not longer than 1000 hours. While sub-atmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of the catalytic reactions.

The EMM-10 family molecular sieve can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The EMM-10 family molecular sieve may be used as an adsorbent, such as for separating at least one component from a mixture of components in the vapor or liquid phase having differential sorption characteristics with respect to the EMM-10 molecular sieve(s) of this disclosure. Therefore, at least one component can be partially or substantially totally separated from a mixture of components having differential sorption characteristics with respect to the EMM-10 molecular sieve(s) of this disclosure by contacting the mixture with the EMM-10 molecular sieve(s) of this disclosure to selectively sorb the one component.

The EMM-10 family molecular sieve is useful as catalyst in a wide range of processes, including separation processes and hydrocarbon conversion processes. Specific examples of hydrocarbon conversion processes which are effectively catalyzed by the EMM-10 molecular sieve(s) of this disclosure by itself or in combination with one or more other catalytically active substances including other crystalline catalysts, include the following:

(i) alkylation of aromatic hydrocarbons, e.g., benzene, with long chain olefins, e.g., $C_{14}$ olefin, with reaction conditions including, individually or in any combination, a temperature of from about 340° C. to about 500° C., a pressure of from about 101 to about 20200 kPa-a (absolute), a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including, individually or in any combination, a temperature of from about 10° C. to about 125° C., a pressure of from about 101 to about 3030 kpa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and di-alkylates with reaction conditions including, individually or in any combination, a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including, individually or in any combination, a temperature of from about 160° C. to about 260° C. and a pressure of from about 2600 to 3500 kPa-a;

(v) alkylation of phenols with olefins or equivalent alcohols to provide long chain alkyl phenols with reaction conditions including, individually or in any combination, a temperature of from about 200° C. to about 250° C., a pressure of from about 1500 to 2300 kpa-a and a total WHSV of from about 2 $hr^{-1}$ to about 10 $hr^{-1}$;

(vi) conversion of light paraffins to olefins and aromatics with reaction conditions including, individually or in any combination, a temperature of from about 425° C. to about 760° C. and a pressure of from about 170 to about 15000 kPa-a;

(vii) conversion of light olefins to gasoline, distillate and lube range hydrocarbons with reaction conditions including, individually or in any combination, a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this disclosure in combination with a Groups 8-10 metal as catalyst with effluent therefrom being reaction in a second stage using zeolite Beta, also in combination with a Groups 8-10 metal, as catalyst, the reaction conditions including, individually or in any combination, a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 $h^{-1}$;

(ix) a combination hydrocracking/dewaxing process in the presence of the MCM-22 family molecular sieve of this disclosure and a hydrogenation component as catalyst, or a mixture of such catalyst and zeolite Beta, with reaction conditions including, individually or in any combination, a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including, individually or in any combination, a temperature of from about 20° C. to about 200° C., a pressure of from 200 to about 20000 kPa-a, a WHSV (gram-olefin per hour gram-zeolite) of from about 0.1 $hr^{-1}$ to about 200 $hr^{-1}$ and an alcohol to olefin molar feed ratio of from about 0.1/1 to about 5/1;

(xi) toluene disproportionation with $C_9$+ aromatics as co-feed with reaction conditions including, individually or in any combination, a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 $hr^{-1}$ to about 30 $hr^{-1}$;

(xii) preparation of the pharmaceutically-active compound 2-(4-isobutylphenyl) propionic acid, i.e. ibuprofen, by reacting isobutyl benzene with propylene oxide to provide the intermediate 2-(4-isobutylphenyl) propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene;

(xvi) in a process for decreasing the durene content of a 90-200° C.+ bottoms fraction obtained from the catalytic conversion of methanol to gasoline which comprises contacting the durene-containing bottoms fraction with hydrogen over a catalyst of the present MCM-22 family molecular sieve with a hydrogenation metal, at conditions including, individually or in any combination, a temperature of from about 230° C. to about 425° C. and a pressure of from about 457 to about 22000 kPa-a;

(xvii) in a processes for co-producing phenol and ketones that proceed through benzene alkylation, followed by formation of the alkylbenzene hydroperoxide and cleavage of the alkylbenzene hydroperoxide into phenol and ketone, e.g., benzene and propylene to phenol and acetone, benzene and $C_4$ olefins to phenol and methyl ethyl ketone, such as those described for example in international application PCT/EP2005/008557, which can be followed by conversion of phenol and acetone to bis-phenol-A as described in international application PCT/EP2005/008554, benzene to phenol and cyclohexanone, or benzene and ethylene to phenol and methyl ethyl ketone, as described for example in PCT/EP2005/008551;

(xviii) in a process of benzene alkylation reactions where selectivity to the monoalkylbenzene is required, e.g., selectively sec-butylbenzene from benzene and $C_4$ olefin feeds that are rich in linear butenes, as described in international application PCT/EP2005/008557, preferably, this conversion is carried out by co-feeding benzene and the $C_4$ olefin feed with the catalyst of the present invention, at a temperature of about 60° C. to about 260° C., for example of about 100° C. to 200° C., a pressure of 7000 kPa-a or less, and a feed weight hourly space velocity (WHSV) based on $C_4$ alkylating agent of from about 0.1 to 50 h$^{-1}$ and a molar ratio of benzene to $C_4$ alkylating agent from about 1 to about 50;

(xix) in a process for transalkylations, such as, for example, polyalkylbenzene transalkylations;

(xx) in a process for conversion of light paraffins to aromatics and olefins with reaction conditions including a temperature from about 375° C. to about 760° C. and a pressure from about 10 to about 20000 kPa-a;

(xxi) in a process for conversion of light olefins to aromatics with reaction conditions including a temperature from about 175° C. to about 760° C. and a pressure from about 100 to about 20000 kPa-a;

(xxii) in a process for conversion of naphtha, e.g., $C_6$-$C_{10}$, and similar mixtures to highly aromatic mixtures with reaction conditions including a temperature in the range of from about 400° C. to 600° C., preferably 480° C. to 550° C., a pressure in the range from 100 kPa-a to 4000 kPa-a, and liquid hourly space velocities (LHSV) ranging from 0.1 to 15 hr$^{-1}$;

(xxiii) in a process for dehydrogenation of cycloaliphatics having 6 member rings with reaction conditions including a temperature of from about 300° C. to about 700° C., a pressure of from about 10 to about 1000 kPa-a, a weight hourly space velocity of from about 0.1 hr$^{-1}$ to about 20 hr$^{-1}$;

(xxiv) in a process for conversion of alcohols, e.g., methanol, or ethers, dimethylether, or mixtures thereof to aromatics. Typical reaction conditions include a temperature of from about 275° C. to about 600° C., a pressure of from about 50 to about 5000 kPa-a, a LHSV of from about 0.5 hr$^{-1}$ to about 50 hr$^{-1}$. Examples of such processes are disclosed in U.S. Pat. No. 4,088,706, which is hereby incorporated by reference; and (xxv) in a process for dehydration of alcohols to form aromatics, such as the dehydration of cyclohexane-triol to form benzene.

Non-limiting examples of aromatic compounds that can be converted to different aromatic compounds by the process of the present invention include the following:

(A) monocyclic alkylaromatic compounds represented by the formula I:

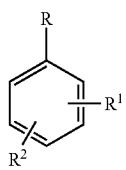

wherein:

R, $R^1$, and $R^2$ are independently selected from the group consisting of hydrogen and an alkyl or alkenyl group having 1 to about 12 carbon atoms, and, preferably 1 to 4 carbon atoms; and, (B) bicyclic alkylaromatic compounds represented by the formula II:

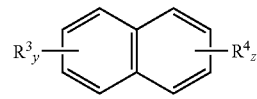

wherein:

$R^3$ and $R^4$ are independently selected from the group consisting of hydrogen and an alkyl or alkenyl group having 1 to about 12 carbon atoms, and, preferably 1 to 4 carbon atoms:

y is an integer of from 0 to 2; and z is an integer of from 0 to 2.

Examples of R, $R^1$, $R^2$, $R^3$, and $R^4$ include straight or branch chained alkyl and alkenyl groups. Examples of such groups include methyl, ethyl, ethylene, n-propyl, isopropyl, propylene, n-butyl, isobutyl, butylene or any combination thereof. The preferred group is methyl.

Examples of monocyclic alkylaromatic compounds corresponding to formula I include, for example, benzene, toluene ethylbenzene, styrene, xylenes such as para-xylene, ortho-xylene, and meta-xylene, diethylbenzenes such as 1,4-diethylbenzene, 1,2-diethylbenzene, and 1,3-diethylbenzene, trimethylbenzenes such as mesitylene (1,3,5-trimethylbenzene), hemimellitene (1,2,3-trimethylbenzene), and pseudocumene (1,2,4-trimethylbenzene), ethyltoluenes, triethylbenzenes such as 1,3,5-triethylbenzene, methylpropylbenzenes, ethylpropylbenzenes, dipropylbenzenes, diisopropylbenzenes, triisopropylbenzenes, and the like.

Examples of bicyclic alkylaromatic compounds corresponding to formular II include 1-methylnaphthalene, 2-methylnaphthalene, dialkylnaphthalenes such as 1,2-dimethylnaphthalene, 1,2-diethylnaphthalene 2,3-dimethylnaphthalene, 2,3-dipropylnaphthalene 2,6-dimethylnaphthalene, 2,6-dibutyl-naphthalene, and the like.

Examples of aromatic compounds to be converted and resulting products are shown below in the table:

| Aromatics To Undergo Conversion | Non-Aromatic Reactants | Aromatic Product |
|---|---|---|
| Benzene | Ethylene | Ethylbenzene |
| Toluene | Methanol | Xylene isomers |
| Xylene isomers, e.g., 9:73:18 wt. ratio of para:meta:ortho | | Different combination of xylene isomers, e.g. 23:57:20 wt. ratio of para:meta:ortho |
| Toluene | | Benzene and xylenes |
| Benzene | Propylene | Cumene and diisopropylbenzene |
| Toluene | Propylene | Cymene isomers |

Reaction conditions for aromatics conversion include, in general, a temperature of from about 200° C. to about 760° C., a pressure of from about 101.3 kPa-a to about 20000 kPa-a, and a weight hourly space velocity of from about 0.08$^{-1}$ to about 2000 hr$^{-1}$.

Alkylation and Transalkylation Reactions

In another embodiment, this disclosure discloses a process for alkylating an aromatic hydrocarbon with an alkylating agent to produce an alkylated aromatic product, the process comprises contacting the aromatic hydrocarbon and the alkylating agent with the catalyst composition of this disclosure under alkylation conditions effective to alkylate the aromatic hydrocarbon with the alkylating agent to form an effluent comprising the alkylated aromatic product. In some preferred embodiments, the aromatic hydrocarbon comprises benzene, the alkylating agent comprises ethylene, and the alkylated aromatic product comprises ethylbenzene. In other preferred embodiments, the aromatic hydrocarbon comprises benzene, the alkylating agent comprises propylene, and the alkylated aromatic product comprises cumene.

The catalyst composition of this disclosure is also useful catalyst for transalkylations, such as, for example, polyalkylbenzene transalkylations.

Substituted aromatic compounds which may be used for the invention should possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic compounds that may be used for this invention include benzene, naphthalene, anthracene, naphthacene, perylene, coronene, and phenanthrene, with benzene being preferred.

Suitable alkyl substituted aromatic compounds that may be used for this invention include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate streams that may contain substantial quantities of benzene, toluene and/or xylene may be particularly suitable feed for the process of this invention. Although the process is particularly directed to the production of ethylbenzene from polymer grade and dilute ethylene, it is equally applicable to the production of other $C_7$-$C_{20}$ alkylaromatic compounds, such as cumene, as well as $C_6$+ alkylaromatics, such as $C_8$-$C_{16}$ linear and near linear alkylbenzenes.

Suitable alkylating agent(s) that may be used in this invention comprise alkene compound(s) and/or alcohol compound (s), and mixtures thereof. Other suitable alkylating agents that may be useful in the process of this invention generally include any aliphatic or aromatic organic compound having one or more available alkylating aliphatic groups capable of reaction with the alkylatable aromatic compound. Examples of suitable alkylating agents are $C_2$-$C_{16}$ olefins such as $C_2$-$C_5$ olefins, viz., ethylene, propylene, the butenes, and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols, and the pentanols; $C_2$-$C_{20}$ ethers, e.g., $C_2$-$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. It is generally preferred that the alkylating agent has no greater than 5 carbon atoms, more preferably no greater than 3 carbon atoms. Thus the alkylating agent may preferably be selected from the group consisting of $C_2$-$C_5$ olefins and $C_1$-$C_5$ alkanols. The alkylating agent includes a concentrated alkene feedstock (e.g., polymer grade olefins) and a dilute alkene feedstock (e.g., catalytic cracking off-gas).

Suitable alkyl substituted aromatic compounds which may be prepared from the alkylation process of the present invention include toluene, xylene, isopropylbenzene (cumene), normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethyl,anthracene; 9-ethylanthracene; 2-methylanthracene; o-methylanthracene; 9,10-dimethylphenanthrene; and 3-methyl-phenanthrene. Preferably, the alkylated aromatic product comprises monoalkylbenzene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{16}$.

The alkylation reaction is carried out with the alkylatable aromatic compound and the alkylating agent in the reaction zone under alkylation or transalkylation conditions. The alkylation or transalkylation conditions include a temperature of 100 to 285° C. and a pressure of 689 to 4601 kPa-a, preferably, a pressure of 1500 to 3000 kPa-a, a WHSV based on alkylating agent (e.g., alkene) for overall reactor of 0.1 to 10 $hr^{-1}$, preferably, 0.2 to 2 $hr^{-1}$, more preferably, 0.5 to 1 $hr^{-1}$, or a WHSV based on both alkylating agent and alkylatable aromatics for overall reactor of 10 to 100 $hr^{-1}$, preferably, 20 to 50 $hr^{-1}$. The alkylatable aromatic compound is alkylated with the alkylating agent (e.g., alkene) in the presence of an alkylation or transalkylation catalyst in a reaction zone or a plurality of reaction zones. The reaction zone(s) are preferably located in a single reactor vessel, but may include another reaction zone having an alkylation or transalkylation catalyst bed, located in separate vessel which may be a bypassable and which may operate as a reactive guard bed. The catalyst composition used in the reactive guard bed may be different from the catalyst composition used in the reaction zone. The catalyst composition used in the reactive guard bed may have multiple catalyst compositions. At least one reaction zone, and normally each reaction zone, is maintained under conditions effective to cause alkylation of the alkylatable aromatic compound with the alkylating agent in the presence of an alkylation or transalkylation catalyst.

The effluent from the reaction zone comprises the desired alkylated aromatic product, unreacted alkylatable aromatic compound, any unreacted alkylating agent (e.g., alkene, alkene conversion is expected to be at least 90 mol. %, preferably, about 98-99.9999 mol. %) and the alkane component and the other impurities. In one embodiment, at least a portion of the effluent is fed to another reaction zone where an alkylating agent is added for reaction with the unreacted alkylatable aromatic compound with an alkylation or transalkylation catalyst. Furthermore, at least a portion the effluent from any of the reaction zone(s) may be fed directly or indirectly to a transalkylation unit. In some embodiments, the amount of the alkylated aromatic product produced by the process of this disclosure is at least 1 wt. %, preferable at least 5 wt. %, even more preferable at least 10 wt. %, and most preferable at least 20 wt. %, greater than the amount of alkylated aromatic product in a effluent produced by contacting an alumina-bound-catalyst composition having a binder consisting of alumina and same weight ratio of the molecular sieve over the alumina-bound-catalyst composition.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of alkylatable aromatic compound, and optionally at least a portion of the alkylating agent, are passed through the unreactive or reactive guard bed prior to entry into the reaction zone. These guard beds not only serve to affect the desired alkylation reaction, but is also used to remove any reactive impurities in the feeds, such as nitrogen compounds, which could otherwise poison the remainder of the alkylation or transalkylation catalyst. The catalyst in the reactive or unreactive guard bed is therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation.

The reaction zone(s) used in the process of the present invention is typically operated so as to achieve essentially complete conversion of the alkene. However, for some applications, it may be desirable to operate at below 100% alkene conversion. The employment of a separate finishing reactor downstream of the reaction zone(s) may be desirable under certain conditions. The finishing reactor would also contain alkylation or transalkylation catalyst, which could be the same or different from the catalyst used in other reaction zones in the alkylation or transalkylation reactor(s) and may be maintained under at least partially liquid phase or alternately vapor phase alkylation or transalkylation conditions. The polyalkylated aromatic compounds in the effluents may be separated for transalkylation with alkylatable aromatic compound(s). The alkylated aromatic compound is made by transalkylation between polyalkylated aromatic compounds and the alkylatable aromatic compound.

The alkylation or transalkylation reactor(s) used in the process of the present invention may be highly selective to the desired monoalkylated product, such as ethylbenzene, but typically produces at least some polyalkylated species. In one embodiment, the effluent from the final alkylation reaction zone is subjected to a separation step to recover polyalkylated aromatic compound(s). In another embodiment, at least a portion of the polyalkylated aromatic compound is supplied to a transalkylation reactor which may be separate from the alkylation reactor. The transalkylation reactor produces an effluent which contains additional monoalkylated product by reacting the polyalkylated species with an alkylatable aromatic compound. At least a portion of these effluents may be separated to recover the alkylated aromatic compound (monoalkylated aromatic compound and/or polyalkylated aromatic compound).

Particular conditions for carrying out the alkylation of benzene with ethylene at least partially in liquid phase may have a temperature of from about 120 to 285° C., preferably, a temperature of from about 150 to 260° C., a pressure of 689 to 4601 kPa-a, preferably, a pressure of 1500 to 4137 kPa-a, a WHSV based on total ethylene and total catalyst for overall reactor of 0.1 to 10 $hr^{-1}$, preferably, 0.2 to 2 $hr^{-1}$, more preferably, 0.5 to 1 $hr^{-1}$, or a WHSV based on both total ethylene and benzene, and total catalyst for overall reactor of 10 to 100 $hr^{-1}$, preferably, 20 to 50 $hr^{-1}$, and a molar ratio of benzene to ethylene from about 1 to about 10.

Particular conditions for carrying out the at least partially in liquid phase alkylation of benzene with propylene may include a temperature of from about 80 to 160° C., a pressure of about 680 to about 4800 kPa-a; preferably from about 100 to 140° C. and pressure of about 2000 to 3000 kPa-a, a WHSV based on propylene of from about 0.1 about 10 $hr^{-1}$, and a molar ratio of benzene to ethylene from about 1 to about 10.

Where the alkylation system includes a reactive guard bed, it is maintained under at least partial in liquid phase conditions. The guard bed will preferably operate at a temperature of from about 120 to 285° C., preferably, a temperature of from about 150 to 260° C., a pressure of 689 to 4601 kpa-a, preferably, a pressure of 1500 to 4137 kPa-a, a WHSV based on total ethylene and the total amount of catalyst for the overall reactor of 0.1 to 10 $hr^{-1}$, preferably, 0.2 to 2 $hr^{-1}$, more preferably, 0.5 to 1 $hr^{-1}$, or a WHSV based on both total ethylene and total benzene, and the total amount of catalyst for the overall reactor of 10 to 100 $hr^{-1}$, preferably, 20 to 50 $hr^{-1}$, and a molar ratio of benzene to ethylene from about 1 to about 10.

The transalkylation reaction may take place under at least partially in liquid phase conditions. Particular conditions for carrying out the at least partially in liquid phase transalkylation of polyalkylated aromatic compound(s), e.g., polyethylbenzene(s) or polyisopropylbenzene(s), with benzene may include a temperature of from about 100° to about 300° C., a pressure of 696 to 4137 kpa-a, a WHSV based on the weight of the polyalkylated aromatic compound(s) feed to the alkylation reaction zone of from about 0.5 to about 100 $hr^{-1}$ and a molar ratio of benzene to polyalkylated aromatic compound (s) of from 1:1 to 30:1, preferably, 1:1 to 10:1, more preferably, 1:1 to 5:1.

In another embodiment, the transalkylation reaction may take place under vapor phase conditions. Particular conditions for carrying out the vapor phase transalkylation of polyalkylated aromatic compound(s), e.g., polyethylbenzene(s) or polyisopropylbenzene(s), with benzene may include a temperature of from about 350 to about 450° C., a pressure of 696 to 1601 kPa-a, a WHSV based on the weight of the polyalkylated aromatic compound(s) feed to the reaction zone of from about 0.5 to about 20 $hr^{-1}$, preferably, from about 1 to about 10 $hr^{-1}$, and a molar ratio of benzene to polyalkylated aromatic compound(s) of from 1:1 to 5:1, preferably, 2:1 to 3:1.

Process for Decreasing Bromine-Reactive Contaminants in Hydrocarbon Feed

Hydrocarbon feeds, such as aromatic hydrocarbon feeds, are derived from processes such as naphtha reforming and thermal cracking (pyrolysis) and can be used as feedstocks in a variety of petrochemical processes, such as para-xylene production from an aromatic hydrocarbon feedstock containing benzene, toluene and xylene (BTX), toluene disproportionation, xylene isomerization, alkylation and transalkylation. However, aromatic hydrocarbon feedstocks often contain contaminants comprising bromine-reactive compounds including unsaturated hydrocarbons, such as mono-olefins, multi-olefins and styrenes, which can cause undesirable side reactions in these downstream processes. Therefore, these contaminants should be removed from the aromatic hydrocarbon feedstocks before they can be used in other processes.

Improved processes for aromatics production, such as that described in the Handbook of Petroleum Processing, McGraw-Hill, New York 1996, pp. 4.3-4.26, provide increased aromatics yield, but also increase the amount of contaminants. For example, the shift from high-pressure semi-regenerative reformers to low-pressure moving bed reformers results in a substantial increase in bromine-reactive components in the reformate streams, which are aromatic hydrocarbon feedstocks for downstream processes. This, in turn, results in a greater need for more efficient and less expensive methods for removal of bromine-reactive contaminants from aromatic hydrocarbon feedstocks, e.g., reformate streams.

Undesirable hydrocarbon contaminants containing olefinic bonds are quantified by the Bromine Index (BI). The number of grams of bromine absorbed by 100 grams of a hydrocarbon or a hydrocarbon mixture indicates the percentage of double bonds present. Thus, when the type and molecular weight is known, the contents of the olefin can be calculated. The Bromine Indices (i.e., numbers) of the hydrocarbon feeds and products are measured to determine the change in composition. Molecular sieves and clay treating have been used to reduce the Bromine Indices of various hydrocarbon products.

The treatment of hydrocarbons to remove olefinic materials from the hydrocarbons using clay catalysts is widely practiced in the petroleum and petrochemical industries One of the most common reasons for this treatment is to remove olefinic materials in order to meet various quality specifications. As used herein, the term "olefinic material" or "olefinic compound" includes both mono-olefins and multi-olefins. The term "mono-olefins" means olefinic compounds containing one carbon-carbon double bond per molecule. Examples of mono-olefins are ethylene, propylene, butenes, hexenes, and octenes. The term "multi-olefins" means olefinic compounds containing at least two carbon-carbon double bonds per molecule. Examples of multi-olefins are butadienes, cyclopentadienes, and isoprenes.

Olefinic compounds may be objectionable in aromatic hydrocarbons at even very low concentrations of less than a few parts per million by weight (wppm) for some processes. For example, in the manufacture of nitration grade aromatics including benzene, toluene and xylenes, it is essential to remove these olefinic materials from the feedstock.

Molecular sieves have been recently proposed as catalysts for removal of olefinic materials from hydrocarbon feedstocks. For example, U.S. Pat. No. 6,368,496 involves the removal of olefinic materials from an aromatic feed using an acid-active catalyst, such as a catalyst comprising a crystalline molecular sieve with ring structures of ten to twelve members or greater.

Molecular sieves catalysts have certain advantages over clay catalysts in the removal olefinic material from hydrocarbon feeds. For example, molecular sieves catalysts usually have a longer operating cycle than clay catalysts, which results in fewer catalyst change-outs and resultant equipment downtime. In addition, the longer operating cycle of molecular sieve catalyst results in the disposal of less catalyst waste. On the other hand, molecular sieve catalysts are considerably more expensive that clay catalysts. Therefore, it is important for economic viability, that molecular sieve catalysts used in the removal of olefinic material from hydrocarbon feeds, have good activity maintenance.

The hydrocarbon feed used in the process of the present invention may contain nitrogen-containing or sulfur-containing impurities that can reduce the cycle length of the catalyst. These impurities are preferably at least partially removed from the hydrocarbon feed before contacting the feed with the catalyst used in the process of the present invention. The feed may be subjected to chemical processes, such as, distillation, fractionation, adsorption, drying, inert gas purging, or pretreatment processes (e.g., distillation, fractionation, water washing, adsorption, drying, inert gas purging, or catalytic reactions) to remove at least a portion of the impurities. For example, the hydrocarbon feed can be contacted with an absorbent under absorption conditions effective to remove at least a portion of such nitrogen-containing or sulfur-containing impurities. Examples of suitable absorbents include clay materials such as the clay materials previously described herein or an alumina compounds ($Al_2O_3$), such as Selectsorb that may be obtained from Moltan Sorbent Technologies. Preferred absorption conditions include a temperature of from ambient to 500° C., more preferably from ambient to 200° C., or most preferably from ambient to 100° C.; a pressure sufficient to maintain liquid phase conditions; a weight hourly space velocity from 0.5 $hr^{-1}$ to about 100 $hr^{-1}$, more preferably from about 0.5 $hr^{-1}$ to about 10 $hr^{-1}$, most preferably from 1.0 $hr^{-1}$ to 4.0 $hr^{-1}$ depending on the hydrocarbon feed being treated.

A wide variety of hydrocarbon feedstocks can be used in the practice of the invention. Examples of suitable hydrocarbon feedstocks include aromatic streams obtained from reforming and cracking processes. These feedstocks can include a wide variety of hydrocarbons, e.g., paraffins, aromatics, and bromine-reactive compounds such as olefins. Usually aromatic hydrocarbon feedstocks include mononuclear aromatic hydrocarbons and undesirable olefins including mono-olefins, multi-olefins, and styrene, which have an initial BI from about 100 to about 3000.

Because the exact nature of the unsaturated hydrocarbons may vary and may even be unknown, indirect methods of measuring the unsaturated hydrocarbons are typically used. One well-known method of measuring trace amounts of unsaturated hydrocarbons is the BI. The measurement of BI is described in detail in ASTM D2710-92, the entire contents of which are incorporated herein by reference. The BI indirectly measures the olefin content of aromatic containing hydrocarbon samples using potentiometric titration. Specifically, the BI is defined as the number of milligrams of bromine consumed by 100 grams of hydrocarbon sample under given conditions.

The aromatics include, for example, benzene, toluene, xylene, ethylbenzene, cumene and other aromatics derived, e.g., from reformate. Reformate is separated by distillation into light reformate (mostly benzene and toluene), and heavy reformate (including toluene, ortho-, meta- and para-xylenes and other heavier aromatics such as $C_9+$). After extraction, the aromatic feedstream typically contains greater than about 98 wt. % benzene and toluene and wppm levels of extraction solvents. Heavy reformate feedstocks typically contain less than about 0.5 wt. % toluene and less than about 250 wppm benzene. Some aromatic streams such as heavy reformate derived from semi-regen and CCR reforming processes contain multi-olefins as they emerge from the processing.

The amount of multi-olefins in a hydrocarbon feedstock may vary from less than 10 wt. %, preferably less than 1 wt.

%, more preferably less than 500 wppm depending on the source of feedstock and any pre-treatment. Extracted benzenes and heavy reformates typically contain less than about 1000 wppm multi-olefins.

The hydrocarbon feedstocks to be processed according to the invention contain bromine-reactive hydrocarbon compounds from about 0.001 to about 10 wt. %, preferably from about 0.001 to about 1.5 wt. %, more preferably from about 0.005 to about 1.5 wt. % or a BI from about 2 to about 20000, preferably from about 2 to about 3000, more preferably from about 10 to about 3000 or most preferably at least 5.

The hydrocarbon feedstock processed according to the present invention will have a lower BI than the initial BI of the hydrocarbon feedstock. Usually after treatment, the BI will be no greater than 50% of the BI value before treatment of hydrocarbon feedstock. Preferably, the BI value will be no greater than 30%, and, more preferably, the BI will be no greater than 20%.

Because of the longer cycle-length of the molecular sieve catalyst, the present invention can usually process hydrocarbon feeds (reduce BI) for longer times between catalyst change out. The term "cycle-length" means the on-oil time of the catalyst before change-out or regeneration.

The present invention usually has a hydrocarbon feed flow-rate of at least 10 kg per day, preferably more than at least 100 kg per day, more preferably at least 200 kg per day.

The process of the present invention is carried out under conditions effective in the remove multi-olefins and mono-olefins from hydrocarbon feed. Exemplary conversion conditions include a temperature of from about 38° C. (100° F.) to about 538° C. (1000° F.), preferably 93° C. (200° F.) to about 371° C. (700° F.), more preferably 93° C. (200° F.) to about 316° C. (600° F.), to a pressure of from about 136 kPa-a (5 psig) to about 13891 kpa-a (2,000 psig), preferably from about 205 kPa-a (15 psig) to about 6996 kPa-a (1000 psig), more preferably from about 205 kPa-a (15 psig) to about 3549 kPa-a (500 psig), a weight hourly space velocity (WHSV) from about 0.1 $hr^{-1}$ and about 200 $hr^{-1}$, preferably from about 1 $hr^{-1}$ and about 100 $hr^{-1}$, more preferably from about 2 $hr^{-1}$ and about 50 $hr^{-1}$. The WHSV is based on the total weight of catalyst, i.e., the total weight of active catalyst plus any binder that is used.

Process of Making Sec-Butyl-Benzene

Sec-butylbenzene is useful as a starting material for the production of phenol and methyl ethyl ketone through the steps of air oxidation to the corresponding hydroperoxide followed by cleavage of the hydroperoxide. Phenol can be used as a solvent and in the production of phenol resins, bisphenol A, ∈-caprolactam, adipic acid, alkyl phenols, and plasticizers, whereas methyl ethyl ketone can be used as a solvent for lacquers and resins and for dewaxing of lubricating oils.

The conventional route for the production of sec-butylbenzene involves alkylation of benzene with n-butene over a homogeneous catalyst, such as $AlCl_3$ or solid phosphoric acid. The product of the alkylation reaction is a mixture containing mainly sec-butylbenzene (S-BB), isobutylbenzene (IBB), tert-butylbenzene, dibutylbenzenes (DS-BB), and tributylbenzenes (TS-BB). Of these compounds, dibutylbenzenes and tributylbenzenes are separated from the reaction mixture and can then transalkylated into sec-butylbenzene.

However, the boiling points of isobutylbenzene, sec-butylbenzene and tert-butylbenzene are 172.8° C., 173.5° C. and 169° C., respectively, and hence it is difficult to separate these compounds from each other by distillation. Moreover, isobutylbenzene and tert-butylbenzene are known to be inhibitors to the oxidation of sec-butylbenzene to the corresponding hydroperoxide. For example, the rate of oxidation of sec-butylbenzene, when the sec-butylbenzene contains 1% by weight of isobutylbenzene, decreases to about 91% of that when the sec-butylbenzene is free of isobutylbenzene. Similarly, when the isobutylbenzene content is 1.65% by weight, the rate of oxidation decreases to about 86%; when the isobutylbenzene content is 2% by weight, the rate of oxidation decreases to about 84%; and when the isobutylbenzene content is 3.5% by weight, the rate of oxidation decreases to as much as about 82%.

Therefore, in order to ensure the efficiency of the air oxidation step, it is important to minimize the amount of isobutylbenzene and tert-butylbenzene formed as by-products during the alkylation step to produce the sec-butylbenzene.

For example, U.S. Pat. No. 5,059,736 describes a process for producing sec-butylbenzene from benzene and n-butene, comprising reacting benzene and n-butene in the presence of a homogeneous liquid aluminum chloride complex catalyst, the catalyst comprising aluminum chloride, hydrogen chloride, and an aromatic hydrocarbon, wherein the amount of aluminum chloride used as a component of the complex catalyst is from 0.51 to 5% by weight of the benzene used, the reaction temperature is from 20° C. to 70° C., and the amount of isobutylbenzene formed as a by-product is such that the weight ratio of isobutylbenzene to sec-butylbenzene formed is not more than 0.01:1. However, as discussed above, even isobutylbenzene impurities of 1 wt % significantly inhibit the oxidation of sec-butylbenzene to the corresponding hydroperoxide.

U.S. Pat. No. 4,992,606 discloses a process for preparing short chain alkyl aromatic compounds which comprises contacting at least one alkylatable aromatic compound with at least one alkylating agent possessing an aliphatic group having from 1 to 5 carbon atoms under alkylation reaction conditions and in the presence of an alkylation catalyst to provide an alkylated aromatic product possessing at least one alkyl group derived from the alkylating agent, the catalyst comprising a synthetic porous crystalline material known as MCM-22. Similar disclosures are contained in U.S. Pat. Nos. 5,371, 310 and 5,557,024 but where the synthetic porous crystalline material is MCM-49 and MCM-56 respectively.

U.S. Pat. No. 5,334,795 discloses a process for the production of ethylbenzene comprising alkylating benzene with ethylene under liquid phase conditions in the presence of a solid, porous acidic alkylation catalyst comprising MCM-22.

International Patent Application No. PCT/US2003/038709, published as WO 2004/052810 discloses a method for alkylating benzene with ethylene in the presence of metal-impregnated MCM-22. The catalysts are selective for mono-ethylbenzene over di- or tri-ethylbenzene.

In an article entitled "Catalytic Properties of Palladium-Zeolite Systems in the Synthesis of Sec-Butylbenzene from Benzene and Ethylene", Inst Org. Khim. im N. D. Zelinskogo, Moscow, Russia, Neftekhimiya (1994), 34(2), 151-70, Isakov et al. report that various palladium-containing zeolites (HY, cation-exchanged or dealuminated Mn+NaY, H-pentasil) are effective in the alkylation of benzene with ethylene to produce predominantly sec-butylbenzene or sec-butylbenzene. However, the article also reports that the product contains $C_4$-$C_6$ alkenes.

The EMM-10 family molecular sieve may be used in a process for producing sec-butylbenzene comprising contacting a feed comprising benzene and ethylene under alkylation conditions with catalyst comprising an EMM-10 family molecular sieve.

Conveniently, the sec-butylbenzene in the alkylation effluent contains less than 0.5 wt %, for example less than 0.1 wt %, such as less than 0.05 wt %, of isobutylbenzene and tert-butylbenzene.

Conveniently, the molecular sieve comprises a metal. Conveniently, the metal is palladium. In one embodiment, the metal is present in an amount of at least 0.5% by weight of the catalyst.

Conveniently, the benzene and ethylene are contacted with the catalyst at a benzene:butene molar ratio between about 10:1 and about 1:10, such as between about 4:1 and about 1:4, for example between about 4:1 and about 1:1.

In one embodiment, the contacting is conducted under at least partial liquid phase conditions. Conveniently, the alkylation conditions include a temperature of from about 0° C. to about 350° C., such as from about 30° C. to about 300° C., a pressure of from about 10 to about 10,000 kPa, and an ethylene weight hourly space velocity (WHSV) of from about 0.1 to about 10 hr$^{-1}$.

In one embodiment, the sec-butylbenzene alkylation effluent comprises polybutylbenzenes and the process further comprises contacting the polybutylbenzenes with benzene in the presence of a transalkylation catalyst to produce sec-butylbenzene. Conveniently, the transalkylation catalyst comprises at least one of zeolite beta, mordenite, USY, MCM-68, MCM-22, PSH-3, SSZ-25, ERB-1, ITQ-1, ITQ-2, MCM-36, MCM-49, MCM-56, UZM-8, and EMM-10 family molecular sieve.

In some embodiments, this disclosure relates to:

Paragraph 1. A process for hydrocarbon conversion comprising contacting, under conversion conditions, a feedstock suitable for hydrocarbon conversion with a catalyst comprising an EMM-10 family molecular sieve.

Paragraph 2. The process recited in Paragraph 1, wherein said EMM-10 family molecular sieve is EMM-10.

Paragraph 3. The process recited in paragraph 1 or 2, wherein said hydrocarbon conversion is aromatic conversion.

Paragraph 4. The process recited in any preceding paragraph, wherein said hydrocarbon conversion is process for alkylating an aromatic hydrocarbon with an alkylating agent to produce an alkylated aromatic product, said process comprising:
contacting said aromatic hydrocarbon and said alkylating agent with the catalyst of paragraph 1 under alkylation conditions effective to alkylate said aromatic hydrocarbon with said alkylating agent to form an effluent comprising said alkylated aromatic product, wherein said alkylated aromatic product comprises monoalkylated aromatic compound and polyalkylated aromatic compound.

Paragraph 5. The process of paragraph 4, wherein said aromatic hydrocarbon comprises benzene, said alkylating agent comprises ethylene, and said alkylated aromatic product comprise ethylbenzene.

Paragraph 6. The process of paragraph 4 or 5, wherein said aromatic hydrocarbon comprises benzene, said alkylating agent comprises propylene, and said alkylated aromatic product comprise cumene.

Paragraph 7. The process of any one of paragraphs 4-6, wherein said aromatic hydrocarbon comprises benzene, said alkylating agent comprises butene, and said alkylated aromatic product comprise sec-butylbenzene.

Paragraph 8. The process of any one of paragraphs 4-7, further comprising steps of:
separating said polyalkylated aromatic compound from said effluent; and
contacting said polyalkylated aromatic compound with an alkylating agent under transalkylation conditions.

Paragraph 9. The process recited in any preceding paragraph, wherein said hydrocarbon conversion comprises a process of removing bromine-reactive contaminates in a hydrocarbon feedstock.

Paragraph 10. The process recited in paragraph 9, wherein the hydrocarbon feed has a multi-olefin level of less than 500 wppm.

Paragraph 11. The process recited in any preceding paragraph, wherein said hydrocarbon conversion is carried at conditions comprising a temperature of from about 200° C. to about 760° C., a pressure of from about 101 kpa-a to about 20000 kpa-a, and a weight hourly space velocity of from about 0.08 to about 2000 hr$^{-1}$.

Paragraph 12. The process recited in Paragraph 11, wherein said aromatics conversion comprises converting feedstock comprising aromatic compounds to a product comprising aromatic compounds which differ from said feedstock.

Paragraph 13. The process recited in Paragraph 12, wherein said feedstock comprises at least one aromatic compound selected from the group consisting of:

(A) monocyclic alkylaromatic compounds represented by the formula:

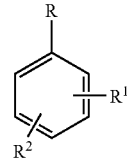

wherein:
R, $R^1$, and $R^2$ are independently selected from the group consisting of hydrogen and an alkyl or alkenyl group having 1 to about 12 carbon atoms, and, preferably 1 to 4 carbon atoms; and (B) bicyclic alkylaromatic compounds represented by the formula:

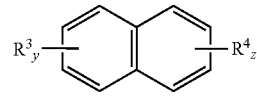

wherein:
$R^3$ and $R^4$ are independently selected from the group consisting of hydrogen and an alkyl or alkenyl group having 1 to about 4 carbon atoms;
y is an integer of from 0 to 2; and
z is an integer of from 0 to 2.

Paragraph 14. The process recited in Paragraph 13, wherein R, $R^1$, $R^2$, $R^3$, and $R^4$ are independently selected from the group consisting of hydrogen, methyl, ethyl, n-propyl, isopropyl, and n-butyl.

Paragraph 15. The process recited in Paragraph 14, wherein said feedstock comprises at least one aromatic compound of formula I and R, $R^1$, $R^2$, $R^3$, and $R^4$ are independently selected from the group consisting of hydrogen, methyl and ethyl.

Paragraph 16. The process recited in Paragraph 15, wherein said feedstock comprises at least one of benzene, toluene ethylbenzene, styrene, xylenes, 1,4-diethylbenzene, 1,2-diethylbenzene, 1,3-1,3,5-trimethylbenzene, 1,2,3-trimethylbenzene, 1,2,4-trimethylbenzene, 1,3,5-triethylbenzene, methylpropylbenzenes, ethylpropylbenzenes, dipropylbenzenes, diisopropylbenzenes, triisopropylbenzenes, 1-methylnaphthalene, 2-methylnaphthalene, 1,2-dimethylnaphthalene, 1,2-diethylnaphthalene 2,3-dimethylnaphthalene, 2,3-dipropylnaphthalene 2,6-dimethylnaphthalene, and 2,6-dibutyl-naphthalene.

Paragraph 17. The process recited in any one of paragraphs 12-16, wherein said at least one aromatic compound present in said feedstock is selected from the group consisting of benzene, toluene, xylenes, and mixtures thereof.

Paragraph 18. The process recited in any one of paragraphs 12-17, wherein said aromatics conversion is selected from the group consisting of the isomerization of dialkyl substituted benzenes, the disproportionation of monoalkyl substituted benzenes, the alkylation of aromatic compounds, the transalkylation of aromatic compounds in the presence of polyalkylaromatic compounds, the dealkylation of alkylaromatic compounds, the isomerization of ethylbenzene to form xylenes, the isomerization of dialkylnaphthalenes.

Paragraph 19. The process recited in Paragraph 18, wherein said aromatics conversion is selected from the group consisting of toluene disproportionation, xylenes isomerization, and aromatics alkylation.

Paragraph 20. The process recited in Paragraph 19, wherein the product comprises at least one of ethylbenzene, cumene, xylene, and sec-butylbenzene.

EXAMPLES

The following examples reflect embodiments of the invention and are by no means intended to be limiting of the scope of the invention.

A sample of EMM-10 was prepared according to example 1 of U.S. patent application Ser. No. 11/824,742. MCM-22 catalyst was prepared according to U.S. Pat. No. 4,954,325, the whole content of which is incorporated herein as reference. MCM-49 catalyst was prepared according to U.S. Pat. No. 5,236,575, the whole content of which is incorporated herein as reference.

Alumina was obtained from UOP LLC (UOP LLC, 25 East Algonquin Road, Des Plaines, Ill. 60017-5017, U.S.A.) as Versal-300 or Versal-200 alumina.

A physical mixture of ammonium exchanged and calcined EMM-10 crystals and alumina, in 80/20 weight ratio, was tested for sec-butylbenzene (s-BB) production. Catalyst performance of EMM-10 was compared with MCM-22 and MCM-49 catalysts also prepared as 80/20 physical mixture.

Example 1

An EMM-10 catalyst was prepared by slurrying a mixture consisting of 80% by weight of EMM-10 and 20% by weight of alumina (Vesral-300) in ammonium nitrate. The solution was then filtered, washed and dried at 120° C. The dried catalyst mixture was placed in a muffle and ramped up in temperature in a flow of air to a maximum of 538° C. The mixture was then pelletized and sized to 14-24 mesh particles. A 0.101 g of this sized catalyst was used for alkylation of benzene with 2-butene in a fixed-bed reactor. The catalyst was diluted with sand to 3 ml and loaded into an isothermal, down-flow, fixed-bed, tubular reactor having an outside diameter of 4.76 mm. The catalyst was dried for 2 hours at 150° C. and 101 kpa-a with 100 ml/min flowing nitrogen. Nitrogen was turned off and benzene was fed to the reactor at 60 ml/hr until reactor pressure reached 2170 kPa-a. Benzene flow was then reduced to 7.63 ml/hr and temperature was adjusted to 160° C. 2-Butene liquid feed (48.66 wt. % cis-butene, 51.07 wt. % trans-butene, 0.05 wt. % n-butane, 0.21 wt. % isobutene and 1-butene, and 0.01 wt. % others) was introduced using a syringe pump at 2.57 ml/hr or 16 hr$^{-1}$ WHSV. Feed benzene/butene molar ratio was 3:1. Liquid products were collected in a cold-trap (25° C. and 101.3 kPa-a) and analyzed off line. Butene conversion was determined by measuring unreacted butene relative to feed butene. Data were collected at 16 then 48 hr$^{-1}$ WHSV on butene at 160° C., 2170 kPa-a, and 3:1 benzene/butene molar ratio. First-order rate constant based on butene conversion and total catalyst weight was 80.2 hr$^{-1}$ for this catalyst. Representative data at 95% butene conversions are shown in Table 1. Representative data at 82% butene conversions are shown in Table 2.

Example 2

A MCM-22 catalyst with a nominal composition of 80 wt. % MCM-22 crystal and 20% Versal 300 alumina was prepared according to the same preparation procedure described in Example 1 with a MCM-22 molecular sieve. The mixture was pelletized and sized to 14-24 mesh particles. A 0.202 g of this sized catalyst was used for s-BB production, following the same procedure described in Example 1. Data were collected at 160° C., 2170 kPa-a, and 3:1 benzene/butene molar ratio with butene flow adjusted to 8, 24, 48 then 8 hr$^{-1}$ WHSV. First-order rate constant based on butene conversion and total catalyst weight was 82.8 hr$^{-1}$ for this catalyst. Representative data at 94% butene conversions are shown in Table 1. Representative data at 82% butene conversions are shown in Table 2.

Example 3

A MCM-49 catalyst with a nominal composition of 80 wt. % MCM-49 crystal and 20 wt. % Versal 300 alumina was prepared according to the same preparation procedure described in Example 1 with a MCM-49 molecular sieve. The mixture was pelletized and sized to 14-24 mesh particles. A 0.201 g of this sized catalyst was used for s-BB production, following the same procedure described in Example 1. Data were collected at 160° C., 2170 kpa-a, and 3:1 benzene/butene molar ratio with butene flow adjusted to 8, 24, 48 then 8 hr$^{-1}$ WHSV. First-order rate constant based on butene conversion and total catalyst weight was 82.8 hr$^{-1}$ for this catalyst. Representative data at 94% butene conversions are shown in Table 1. Representative data at 86% butene conversions are shown in Table 2.

Comparison of Catalyst Performance for s-BB Production

Table 1 compares catalyst performance for s-BB production at 94-95% butene conversion. Table 2 compares catalyst performance for s-BB production at 82-86% butene conversion. When compared with MCM-22 and MCM-49 catalysts for s-BB production, EMM-10 is equally effective with comparable activity and selectivity. EMM-10 appears to have a higher tendency for $C_8^=$ (butene dimers) formation than MCM-22 or MCM-49 catalyst.

TABLE 1

| | Example | | |
|---|---|---|---|
| | 1 | 2 | 3 |
| Days on Stream | 4.8 | 4.8 | 3.8 |
| Benzene WHSV | 66.0 | 99.2 | 99.4 |
| Butene WHSV | 15.8 | 23.8 | 23.8 |
| Butene Conversion, % | 94.9 | 93.9 | 94.2 |

TABLE 1-continued

| | Example | | |
|---|---|---|---|
| | 1 | 2 | 3 |
| Product Selectivity, wt % | | | |
| i-Butane | 0.001 | 0.002 | 0.001 |
| n-Butane | 0.000 | 0.036 | 0.008 |
| $C_5$-$C_7$ | 0.194 | 0.161 | 0.127 |
| $C_8=$ | 3.978 | 2.172 | 1.772 |
| $C_{9-11}$ | 0.165 | 0.146 | 0.126 |
| $C_{12}=+C_{10}$-$C_{11}$ Aromatics | 0.263 | 0.259 | 0.199 |
| $C_{13-15}$ | 0.137 | 0.231 | 0.158 |
| Cumene | 0.030 | 0.034 | 0.035 |
| t-BB | 0.038 | 0.067 | 0.067 |
| i-BB* | 0.000 | 0.000 | 0.000 |
| s-BB | 86.213 | 85.082 | 89.785 |
| n-BB | 0.058 | 0.010 | 0.021 |
| DiBB | 8.451 | 10.877 | 7.262 |
| TriBB | 0.457 | 0.885 | 0.422 |
| Heavies | 0.015 | 0.039 | 0.017 |
| Sum | 100.0 | 100.0 | 100.0 |
| s-Butylbenzene (BB) Purity, | | | |
| t-BB/all BB, % | 0.044 | 0.078 | 0.075 |
| i-BB*/all BB, % | 0.000 | 0.000 | 0.000 |
| s-BB/all BB, % | 99.889 | 99.910 | 99.902 |
| n-BB/all BB, % | 0.067 | 0.012 | 0.024 |
| Sum, % | 100.0 | 100.0 | 100.0 |
| Di-BB/s-BB Wt Ratio, % | 9.8 | 12.8 | 8.1 |
| 1st-order rate constant, $hr^{-1}$ | 80.2 | 82.8 | 93.4 |

*iso-Butylbenzene less than 0.5% in total butylbenzene is not detectable with our GC.

TABLE 2

| | Example | | |
|---|---|---|---|
| | 1 | 2 | 3 |
| Days on Stream | 5.5 | 5.1 | 4.0 |
| Benzene WHSV | 198.1 | 198.5 | 198.8 |
| Butene WHSV | 47.5 | 47.6 | 47.7 |
| Butene Conversion, % | 81.64 | 82.05 | 85.6 |
| Product Selectivity, wt % | | | |
| i-Butane | 0.000 | 0.002 | 0.002 |
| n-Butane | 0.629 | 0.425 | 0.346 |
| $C_5$-$C_7$ | 0.215 | 0.187 | 0.154 |
| $C_8=$ | 5.469 | 2.819 | 2.316 |
| $C_{9-11}$ | 0.133 | 0.193 | 0.095 |
| $C_{12}=+C_{10}$-$C_{11}$ Aromatics | 0.177 | 0.260 | 0.174 |
| $C_{13-15}$ | 0.049 | 0.183 | 0.116 |
| Cumene | 0.019 | 0.034 | 0.029 |
| t-BB | 0.010 | 0.049 | 0.039 |
| i-BB* | 0.000 | 0.000 | 0.000 |
| s-BB | 86.143 | 84.778 | 89.932 |
| n-BB | 0.049 | 0.045 | 0.010 |
| DiBB | 6.831 | 10.257 | 6.492 |
| TriBB | 0.270 | 0.736 | 0.280 |
| Heavies | 0.006 | 0.031 | 0.016 |
| Sum | 100.0 | 100.0 | 100.0 |
| s-Butylbenzene (BB) Purity, | | | |
| t-BB/all BB, % | 0.012 | 0.058 | 0.043 |
| i-BB*/all BB, % | 0.000 | 0.000 | 0.000 |
| s-BB/all BB, % | 99.931 | 99.889 | 99.945 |
| n-BB/all BB, % | 0.057 | 0.053 | 0.011 |
| Sum, % | 100.0 | 100.0 | 100.0 |
| Di-BB/s-BB Wt Ratio, % | 7.9 | 12.1 | 7.2 |
| 1st-order rate constant, $hr^{-1}$ | 80.2 | 82.8 | 93.4 |

*iso-Butylbenzene less than 0.5% in total butylbenzene is not detectable with our GC.

Example 4

1.51 grams of catalyst made in example 1 was mixed with 3.21 grams of 80/120 mesh sand and tested for alkylation of benzene with propylene in a fixed-bed reactor. The catalyst and sand was loaded into an isothermal, down-flow, fixed-bed, tubular reactor having an outside diameter of 4.76 mm. The catalyst was dried at 130° C. and 2170 kPa-a in flowing benzene at 8.92 ml/hr. Liquid propylene feed was introduced from an ISCO pump at 2.48 ml/hr. Feed benzene/propylene molar ratio was 3:1. Liquid products were collected in a cold-trap (25° C. and 101.3 kPa-a) and analyzed off line. The results show that the EMM-10 catalyst has DiPB/Cumene around 10 wt. % for benzene/propylene molar ratio 3:1, temperature 130° C. and pressure 2170 kPa-a and about 20 wt. % for benzene/propylene molar ratio 1.5:1, temperature 130° C. and pressure 2170 kPa-a Examples 5-6

Testing Procedures

Feed Pretreatment

Benzene (99.96 wt. %) was obtained from the ExxonMobil Baytown Chemical plant. The benzene was passed through a pretreatment vessel (2 L Hoke vessel) containing absorbent materials from inlet to outlet. All absorbent feed pretreatment materials were dried in a 260° C. oven for 12 hours before using.

Polymer grade propylene was obtained from Scott Specialty Gases (Pasadena, Tex., USA). Propylene was passed through a 300 ml vessel containing absorbents which were dried in a 260° C. oven for 12 hours before using.

Ultra high purity grade Nitrogen was obtained from Scott Specialty Gases. Nitrogen was passed through a 300 ml vessel containing absorbents which were dried at 260° C. for 12 hours before using.

One gram of catalyst was dried in air at 260° C. for 2 hours. The catalyst was removed immediately after drying. The bottom of a catalyst basket was packed with quartz chips followed by loading of 0.1 gram or 0.5 grams of catalyst into basket on top of the quartz chips. The catalyst was then covered by additional quartz chips. The catalyst basket containing the catalyst and quartz chips was dried at 260° C. in air for about 16 hours.

Before each experiment the reactor and all lines were cleaned with a suitable solvent (such as toluene) followed by flowing of air after cleaning to remove all cleaning solvent. The catalyst basket containing the catalyst and quartz chips was placed in reactor immediately after drying.

A 300 ml Parr® batch reaction vessel (Series 4563 mini Bench top reactor with a static catalyst basket, Parr Instrument Company, Moline, Ill. USA) equipped with a stir rod and static catalyst basket was used for the activity and selectivity measurements. The reaction vessel was fitted with two removable vessels for the introduction of benzene and propylene respectively.

Catalytic Activity and Selectivity

The activity and selectivity of a catalyst were measured based on benzene alkylation with propylene. Catalytic activity (CAP number) was calculated using the second order rate constant for the formation of cumene under the reaction conditions (temperature 130° C. and pressure 2170 kpa-a) times a constant of 909.09. Reaction rate-constants were calculated using methods known to those skilled in the art. See "Principles and Practice of Heterogeneous Catalyst", J. M. Thomas, W. J. Thomas, VCH, 1st Edition, 1997, the disclosure of which is incorporated herein by reference. Catalyst selectivity was calculated using the weight ratio of cumene produced over di-isopropyl benzenes (DiPB) produced under the reaction conditions (temperature 130° C. and pressure 2170 kPa-a).

The reactor was purged with 100 ml/min of the treated ultra high purity nitrogen, $N_2$, for 2 hours at 170° C. Then, the reactor temperature was reduced to 130° C. under nitrogen flow. All inlets and outlets of the reactor were closed off afterward. Pretreated benzene (156.1 gram) was transferred into the reactor under 791 kPa-a ultra high purity nitrogen blanket. The reactor was stirred at 500 rpm for 1 hour. Pretreated liquid propylene (28.1 gram) under 2170 kPa-a ultra high purity nitrogen is then transferred to the reactor. The reactor was maintained at 2170 kPa-a by the 2170 kPa-a ultra high purity nitrogen. Liquid samples were taken at 15, 30, 60, 120, 180, and 240 min after addition of the propylene.

0.1 gram (example 5) and 0.5 gram (example 6) of catalyst made in example 1 were loaded in a stirred autoclave and tested with a benzene/propylene molar feed of 3:1 for 4 hours at 130° C.

CAP Activity and Selectivity results clearly showed that EMM-10 could alkylate benzene with propylene to produce cumene.

|  | CAP Activity at 1 gram | DiPB selectivity |
|---|---|---|
| Example 5 | 480 | 16.4 wt. % |
| Example 6 | 376 | 15.5 wt. % |

What is claimed is:

1. A process for alkylating an aromatic hydrocarbon with an alkylating agent to produce an alkylated aromatic product, said process comprising:
    contacting said aromatic hydrocarbon and said alkylating agent with a catalyst of under alkylation conditions effective to alkylate said aromatic hydrocarbon with said alkylating agent to form an effluent comprising said alkylated aromatic product, wherein said alkylated aromatic product comprises monoalkylated aromatic compound and polyalkylated aromatic compound, the catalyst comprising an EMM-10 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms.

2. The process recited in claim 1, wherein said EMM-10 family molecular sieve is EMM-10.

3. The process of claim 1, wherein said aromatic hydrocarbon comprises benzene, said alkylating agent comprises ethylene, and said alkylated aromatic product comprise ethylbenzene.

4. The process of claim 1, wherein said aromatic hydrocarbon comprises benzene, said alkylating agent comprises propylene, and said alkylated aromatic product comprise cumene.

5. The process of claim 1, wherein said aromatic hydrocarbon comprises benzene, said alkylating agent comprises butene, and said alkylated aromatic product comprise sec-butylbenzene.

6. The process of claim 1, further comprising steps of:
    separating said polyalkylated aromatic compound from said effluent; and
    contacting said polyalkylated aromatic compound with an alkylating agent under transalkylation conditions.

7. The process recited in claim 1, wherein said alkylation conditions comprising a temperature of from about 200° C. to about 760° C., a pressure of from about 101 kPa-a to about 20000 kPa-a, and a weight hourly space velocity of from about 0.08 to about 2000 hr-1.

8. The process recited in claim 1, wherein said feedstock comprises at least one aromatic compound selected from the group consisting of:
    (A) monocyclic alkylaromatic compounds represented by the formula:

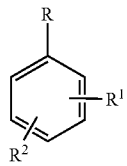

wherein:
R, R1, and R2 are independently selected from the group consisting of hydrogen and an alkyl or alkenyl group having 1 to about 12 carbon atoms, and, preferably 1 to 4 carbon atoms; and
(B) bicyclic alkylaromatic compounds represented by the formula:

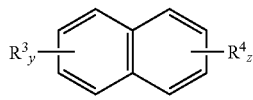

wherein:
R3 and R4 are independently selected from the group consisting of hydrogen and an alkyl or alkenyl group having 1 to about 4 carbon atoms;
y is an integer of from 0 to 2; and
z is an integer of from 0 to 2.

9. The process recited in claim 8, wherein R, R1, R2, R3, and R4 are independently selected from the group consisting of hydrogen, methyl, ethyl, n-propyl, isopropyl, and n-butyl.

10. The process recited in claim 9, wherein said feedstock comprises at least one aromatic compound of formula I and R, R1, R2, R3, and R4 are independently selected from the group consisting of hydrogen, methyl and ethyl.

11. The process recited in claim 10, wherein said feedstock comprises at least one of benzene, toluene ethylbenzene, styrene, xylenes, 1,4-diethylbenzene, 1,2-diethylbenzene, 1,3-1,3,5-trimethylbenzene, 1,2,3-trimethylbenzene, 1,2,4-trimethylbenzene, 1,3,5 -triethylbenzene, methylpropylbenzenes, ethylpropylbenzenes, dipropylbenzenes, diisopropylbenzenes, triisopropylbenzenes, 1-methylnaphthalene, 2-methylnaphthalene, 1,2-dimethylnaphthalene, 1,2-diethylnaphthalene 2,3-dimethylnaphthalene, 2,3-dipropylnaphthalene 2,6-dimethylnaphthalene, and 2,6-dibutyl-naphthalene.

12. The process recited in claim 1, wherein said at least one aromatic compound present in said feedstock is selected from the group consisting of benzene, toluene, xylenes, and mixtures thereof.

* * * * *